United States Patent [19]
Churchouse et al.

[11] Patent Number: 5,310,525
[45] Date of Patent: May 10, 1994

[54] FLUID DETECTION DEVICE

[75] Inventors: Stephen J. Churchouse, Banbury; David J. Fitchett, Daventry, both of United Kingdom; Louis Rey, Lausanne, Switzerland

[73] Assignee: Whatman Scientific Limited, Banbury, England

[21] Appl. No.: 917,044

[22] PCT Filed: Feb. 6, 1991

[86] PCT No.: PCT/GB91/00179
§ 371 Date: Sep. 18, 1992
§ 102(e) Date: Sep. 18, 1992

[87] PCT Pub. No.: WO91/12527
PCT Pub. Date: Aug. 22, 1991

[30] Foreign Application Priority Data
Feb. 8, 1990 [GB] United Kingdom ............... 9002856

[51] Int. Cl.[5] ........................................... G01N 33/00
[52] U.S. Cl. .................................... 422/56; 422/57; 422/58; 422/61; 422/69; 422/87; 422/88
[58] Field of Search .............. 422/56, 57, 58, 68.1, 422/61, 69, 86, 87, 88; 436/169, 170, 902, 162, 807; 435/807

[56] References Cited

U.S. PATENT DOCUMENTS

| | | | |
|---|---|---|---|
| 3,420,205 | 1/1969 | Morison | 422/56 X |
| 4,195,055 | 3/1980 | Patel | 422/56 |
| 4,631,174 | 12/1986 | Kondo | 422/56 |
| 4,772,560 | 9/1988 | Attar | 422/165 |
| 4,921,823 | 5/1990 | Furneaux | 502/439 X |

FOREIGN PATENT DOCUMENTS

| | | |
|---|---|---|
| 1157355 | 11/1983 | Canada . |
| 2507093 | 9/1976 | German Democratic Rep. . |
| 425276 | 5/1967 | Switzerland . |
| 2084725 | 6/1984 | United Kingdom . |

OTHER PUBLICATIONS

EPO Search Report EP 85 30 7159, Appl'n No. 0178831, Dec. 17, 1985.

Primary Examiner—James C. Housel
Assistant Examiner—T. A. Trembley
Attorney, Agent, or Firm—Cooper & Dunham

[57] ABSTRACT

A device of the type which uses a moving boundary for detecting a fluid analyte. The device includes an impervious container (10, 12, 14) having a fluid entry aperture (20) and containing two contiguous layers. One of the layers is a detection layer (16) in the form of a sheet comprising a reagent to generate a signal by a reaction initiated by the analyte. The other layer (18) is a spreading layer permeable by the analyte position such that analyte entering the container spreads within the spreading layer. The device can be used, for example, as a gas monitor for indicating exposure to hazardous gases or vapours.

11 Claims, 4 Drawing Sheets

FLUID DETECTION DEVICE

BACKGROUND OF THE INVENTION

This invention is concerned with devices for detecting a fluid analyte, of the type comprising a mass of porous material containing a reagent that reacts with the analyte to generate a signal, usually a change in color. Such devices may be divided into two classes. In one class, the analyte may be quantified by the rate of color change, or alternatively by the depth of color developed in a given time, the colour being generally uniform over the whole of the detection area. A device of this kind is described in U.S. Pat. No. 4,631,174 (Fuji) and comprises a laminate of a hydrophobic impervious layer with an entry aperture for liquid, a porous spreading layer, a chemical reagent layer (to change color by reaction with analyte in the test liquid), and a support layer. In such devices, access of the analyte to the chemical reagent layer is essentially rapid, and the rate of color generation is determined by the rate of reaction between the analyte and the reagent. A similar device is described in U.S. Pat. No. 4,772,560.

In the other class of devices, the analyte may be quantified by the rate of movement (or by the distance moved in a given time) of a moving boundary. Such a device comprises a mass of detection material, to which analyte gains access in a controlled manner comprising a region that has not been contacted by the analyte, and a region that has been contacted by the analyte, and a moving boundary between the two. The device of this invention is of the moving boundary type.

In environments where exposure to hazardous gases or vapors may occur, it is common practice to use a disposable gas monitor attached to the clothing. Typically these devices are used in industrial manufacture, mining, military and in fire and other emergency services. Length of stain tubes (e.g. sold under the Trademark Drager) are commonly used for this purpose and are commercially available for a wide variety of gases. In essence they consist of a glass tube containing a quantity of silica gel impregnated with chemicals that give a color change in the presence of the gas. When required, one end of the glass tube is snapped open in order to begin exposure of the reactive gel to the atmosphere. Exposure to the monitored gas produces a colored region that increases in length as a result of continued diffusion of the gas into the tube. The tubes are roughly calibrated (logarithmically) in order to give a concentration after one hour of exposure. The silica gel impregnated with reactive chemical, acts both as a diffusion medium and as a detection medium. Although very widely used, the tubes are complicated to manufacture, calibration may vary from tube to tube, and are expensive (for high volume manufacture) and awkward to use. In addition, they are subject to considerable variability in response due to dependence on the convective conditions prevailing.

Passive dosi-tubes are marketed under the Trademark Gastec. This device comprises a diffuser and a chemical reagent parallel in a glass tube whose end is broken open to admit the atmosphere. Silica gel impregnated with chemicals is used as the reagent. The tubes are generally similar to, and suffer from the same disadvantages as, Drager tubes.

U.S. Pat. No. 4,195,055 describes a time-temperature device of the moving-boundary type, but which has no inlet aperture. Also, the same material is used as a spreading medium and a detection medium.

British patent specification 2168480 describes a gas detector comprising a circular disc of detection material contained in a housing having an axial entry aperture whose size and length controls the rate of entry of the gas being detected and the movement of the moving boundary on the disc. There is a relatively large open space within the housing in front of the disc.

British patent specification 2084725 describes a gas detection device comprising a porous strip in a glass tube whose end is broken open to provide access to the atmosphere. Again, the strip is surrounded by a relatively large air gap. Again, the rate of movement of the moving boundary is controlled by the rate of entry of gas into the tube. The device as described in these two British patent specifications suffer from two disadvantages:

The rate of entry of gas into the device is controlled by conditions in the entry aperture, and these may be affected by atmospheric conditions, e.g. if the device is used in a wind or near a fan.

Once inside the device, the gas has relatively unimpeded flow to the detection layer, as a result of which the moving boundary may become blurred.

SUMMARY OF THE INVENTION

The present invention provides a device of the moving boundary type for detecting a fluid analyte, which device comprises an impervious container having a fluid entry aperture and containing two contiguous layers:

a detection layer which is a sheet comprising a reagent to generate a signal by a reaction initiated by the analyte, and a spreading layer permeable by the analyte positioned such that analyte entering the container spreads within the spreading layer, wherein the spreading layer is permeable to an extent which substantially determines, in use of the device, the rate of movement of the moving boundary.

The detection layer may be organic or inorganic. An advantage of inorganic, e.g. metal oxide or porous glass layers is that they may be more resistant than are organic layers to the chemicals and conditions under which the device may be used. The detection layer may be porous in order that fluid analyte from the spreading layer can enter and react with a chemical reagent contained in the pores. For this purpose it is necessary that the pores extend transverse to the plane of the layer. Pores extending longitudinally in the plane of the detection layer are not useful for detection and are not particularly desired, although they are generally not harmful. Or the detection layer may be a non-porous sheet with the reagent on the surface.

A preferred detection layer has pores extending transverse to the layer from one major face to the other. A particularly preferred example of such a layer is a porous anodic aluminium oxide sheet; in this, generally cylindrical pores extend from one face to the other and are not interconnected. Asymmetric anodic membranes as described in EPA 178831 are also useful. In devices according to the invention, such sheets give excellent resolution and excellent sensitivity and color intensity. This latter advantage may result from the fact that the sheets are generally transparent or translucent, so that all colored material in the pores is visible.

An anodic aluminium oxide sheet may be used in a form detached from the aluminium metal substrate on which it was formed. Alternatively, an anodic aluminium oxide sheet may be used as a detection layer while still attached to its metal substrate, and this may simplify construction and sealing of the detection layer within the device. Since the aluminium metal substrate which overlies one face of the anodic oxide sheet is generally opaque, the other face of the anodic oxide sheet needs to be visible. That implies the need to use a spreading layer, overlying that other face, which is transparent or translucent. An air gap is suitable, but other porous translucent layers are possible.

The detection layer comprises a reagent to generate a signal by reaction with the analyte. The nature of the reagent depends on the analyte and is not critical to the invention. Chemical reagents for detecting various different analytes are well known and commercially available, for example in the Drager tubes referred to above. The reagent may be present on the surface of the sheet or more preferably in the pores of the layer, either as a coating on the pore walls or completely filling and blocking the pores. The signal generated by reaction with the analyte is most usually a color change, but may be any other easily observed signal, e.g. generation of a fluorescent compound, or generation of a compound that becomes visible when illuminated in UV light.

The analyte is present in the fluid medium into which the detection device is introduced or brought into contact. Although the invention is applicable to devices for detecting liquid analytes, it is of major importance for detecting gases, e.g. toxic gases in the surrounding atmosphere. The device can be used, for example, to monitor a process in which the analyte is produced, e.g. cooking in which $H_2O$ is produced. By application of different reagents to different areas of the detection layer, the device can be arranged to be capable of simultaneously detecting two or more different analytes.

The spreading layer acts to transport analyte from the entry aperture to the detection layer. Flux through the spreading layer may be achieved by three processes (i) diffusion ii) capillary action and (iii) pumping. In one preferred aspect the device relies solely on diffusion or capillary action. In another aspect, especially when low concentrations of analyte are involved, it may be required to pump the fluid medium through the device from the entry aperture to an outlet. In this case diffusion may be insignificant.

In one embodiment, the spreading layer is a tortuous path porous sheet. Suitable are tape-cast sheets of inorganic e.g. metal oxide particles partly sintered together. Also suitable are sheets of woven or non-woven organic or inorganic fibers. Preferred are sheets of glass fiber filter paper. Various grades of filter paper available from Whatman are satisfactory, cheap, robust, flexible and easily used.

In another embodiment, the spreading layer is a narrow gap adjacent the detection layer. A suitable narrow gap can be provided simply by laying the detection layer on an impervious surface. For example, if one anodic aluminium oxide sheet is placed on top of another, then the narrow gap between them constitutes the spreading layer and one sheet constitutes (or possibly both sheets constitute) the detection layer. By way of another example, if a porous detection layer is placed on top of an impermeable plastic sheet, the narrow gap between the two can constitute a spreading layer.

No matter whether the device is operated in a passive (spreading by diffusion) or a pumped mode, the thickness of the spreading layer is important. If the layer is too thin, there will be insufficient passage of fluid along it and a clear moving boundary will not be generated in the detection layer. If the spreading layer is too thick, then analyte may spread along it without contacting the reagent in the detection layer, and again a clear moving boundary will not be generated. The spreading layer should be such as to permit movement of fluid along it at a convenient rate, but such that reaction between analyte and reagent in the detection layer takes place substantially adjacent the moving boundary. The spreading layer is preferably no more than 5 mm thick, e.g. from 0.1–2.0 mm thick. The inventors have found air gap spreading layers 0.2–1.5 mm thick, and porous spreading layers 0.2–0.8 mm thick, to be particularly convenient.

The spreading layer may comprise two regions, an upstream region adjacent the inlet aperture and a downstream region, with the downstream region being more permeable than the upstream region to the analyte. Analyte entering the device spreads slowly through the upstream region and then more rapidly through the downstream region. This feature enables rate of movement of the moving boundary to be correlated more directly with analyte concentration.

The detection layer and the spreading layer are contiguous, so that analyte in the spreading layer can pass to the detection layer and there react with the reagent to generate a signal. A modifying layer (see below) may be interposed between the spreading layer and the detection layer. It is possible to provide two spreading layers with a detection layer sandwiched between them; or to provide two detection layers with a spreading layer sandwiched between them. If one porous anodic membrane is laid on top of another, then each may act as a detection layer, with the air gap between them constituting a spreading layer. The two detection layers may comprise different reagents to detect different analytes.

In a preferred embodiment, the container comprises two flexible sheets impermeable to the analyte joined round their periphery and enclosing the detection layer and the spreading layer between them. The flexible sheets may be of plastics material, and at least the sheet overlying the detection layer may be made transparent or translucent, so that a moving boundary in the detection layer is clearly observable. The two flexible sheets may be sealed together round their periphery or otherwise bonded so that the complete device resembles a credit card. Preferably the porous sheets constituting the spreading layer and the detection layer are each sealed to the flexible plastic sheet which overlies them, so that spreading of the analyte from the inlet aperture can only take place through the spreading layer.

To avoid risk of migration of analyte round the edges of the spreading layer, rather than through the layer, a gasket may be used. Or either the detection layer or the spreading layer may overlap the other so as to reduce any gap round the edges.

The container is impervious to the analyte. (In practice, the container may be not completely impermeable, but this can be ignored provided that the quantity of analyte entering the container, other than via the entry aperture, is so small as not to materially affect the operation of the device.) Effectively, the analyte can therefore gain entry only through the entry aperture. This may simply be a hole in one or both of the plastic sheets constituting the container. The aperture may be kept closed, e.g. by means of a pealable plastics strip, until the device is to be activated for use. A hydrophobic region may be provided adjacent the entry aperture to the container, in order to exclude water from the detection layer. Or the spreading layer may be made hydrophobic.

It may be convenient to modify the analyte by converting it into some other chemical species, which is then caused to generate a signal by reaction with the reagent in (or on) the detection layer. The modifier may be provided as a layer adjacent the entry aperture, so that reaction with the analyte occurs immediately on, or even prior to, its entry into the container. Or a modifying layer may be provided between the detecting layer and the spreading layer or as an integral part of either the spreading layer or the detection layer. In such cases, the signal in the detection layer is generated by a reaction initiated by the analyte, rather than by reaction with the analyte itself.

The color change or other signal generated in the detection layer forms a boundary which progressively moves away from the aperture. Five features of the device may affect the rate of that movement. These are: the size of the entry aperture; the thickness and longitudinal porosity of the spreading layer; and the thickness and longitudinal porosity of the detection layer. It is preferred that the longitudinal porosity of the spreading layer be greater than that of the detection layer, so that spreading of the analyte takes place mainly or exclusively in the spreading layer. It is also preferred that the porosity of the spreading layer be such as to determine, in use of the device, the rate of movement of the moving boundary. In other words, it is preferred that the entry aperture be sufficiently large and open that a small change in its size does not have any effect on the rate of movement of the moving boundary.

BRIEF DESCRIPTION OF THE DRAWINGS

For presentation of the device, many different geometries are available, some of which are illustrated in the accompanying drawings in which:

FIG. 1b is a section on the line A—A of FIG. 1a;

DETAILED DESCRIPTION OF THE PREFERRED EMBODIMENT

Figure 1A:
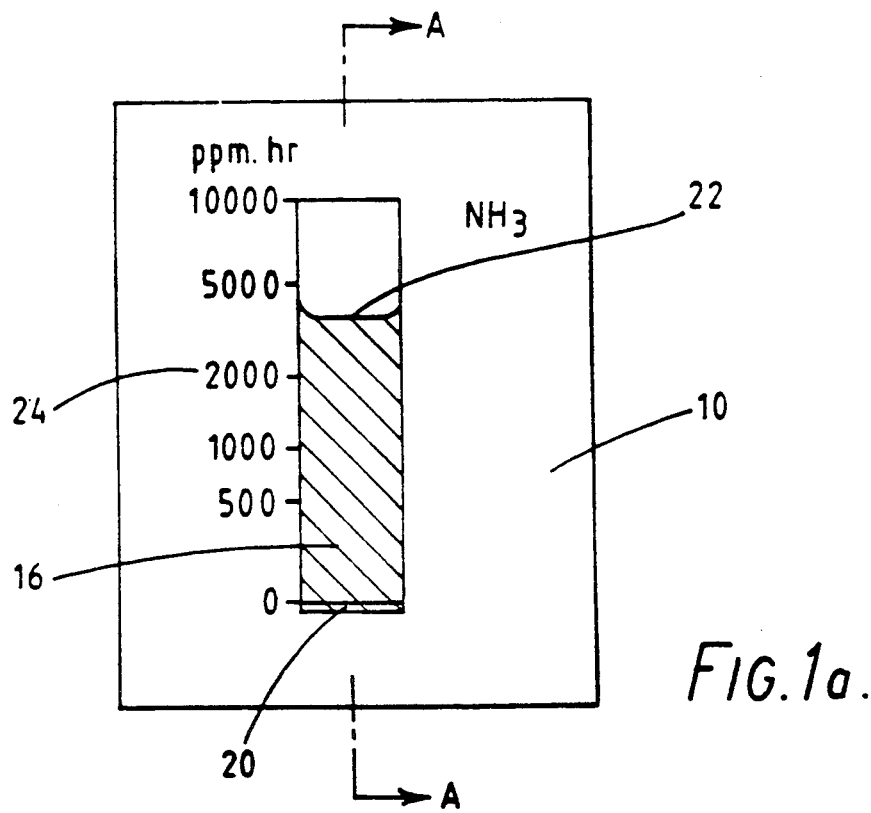
FIG. 1a is a plan view of a preferred device according to the invention.
Figure 1B:
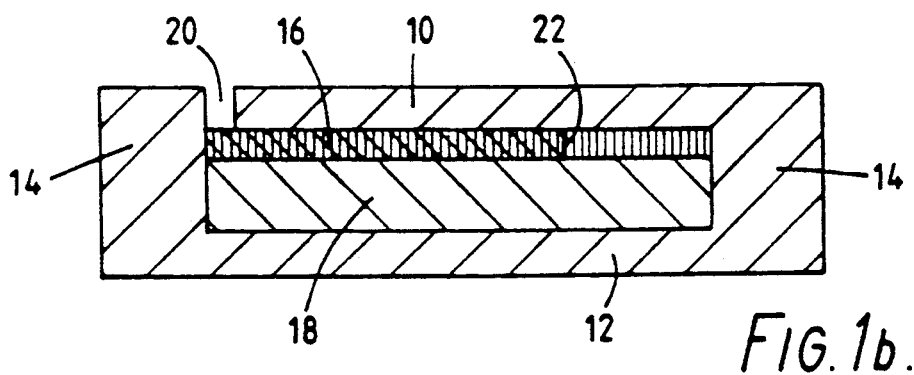

Referring to FIG. 1, a container comprises two flexible sheets 10, 12 of transparent plastics material moulded together at 14 round their periphery. Sandwiched between the two sheets are a porous detection layer 16 and a spreading layer 18. The porous detection layer is an anodic aluminium oxide sheet. The spreading layer is a commercial filter paper. An entry aperture 20 extends through the plastic sheet 10 and gives access to one end of the detection layer. Alternatively, the entry aperture could have been through the plastic sheet 12 giving access to the spreading layer 18 or to both spreading and detection layers.

In order to detect ammonia ($NH_3$) the pores of the anodic sheet 16 have been filled with bromophenol blue by known techniques. The device shown in FIG. 1 has been exposed for 1 hour to an atmosphere containing about 4000 ppm of ammonia. This has generated a dark blue color over most of the detection layer, the remainder of the detection layer remaining yellow and the two regions being separated by a boundary 22 which has moved, during the hour's exposure, from 0 to 4000 on the scale 24 marked on the device.

The devices shown in FIGS. 2 to 5 comprise the same components, namely a porous detection layer 16 overlying a spreading layer 18, the two being enclosed within a plastics housing generally resembling a credit card and being provided with an entry aperture 20. Like reference numbers are used for like parts.

Figure 2:
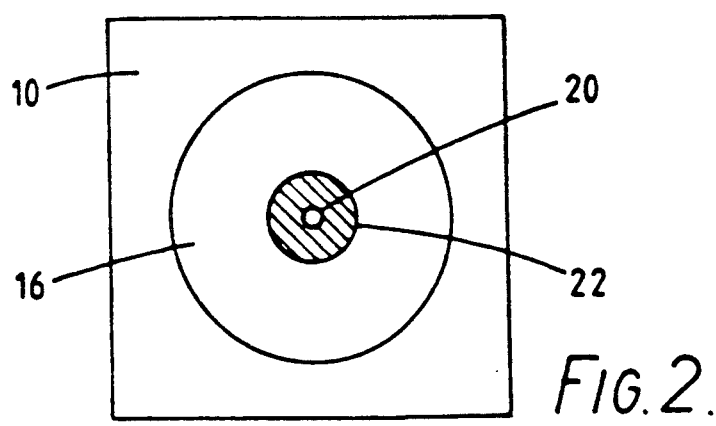
FIGS. 2 to 5 are diagrammatic plan views of alternative devices.

In FIG. 2, the porous detection layer 16 is circular and the entry aperture 20 is positioned at the middle of the circle. This device gives excellent gas sensitivity over lower concentration ranges and is capable of handling a wider range of concentrations.

Figure 3:
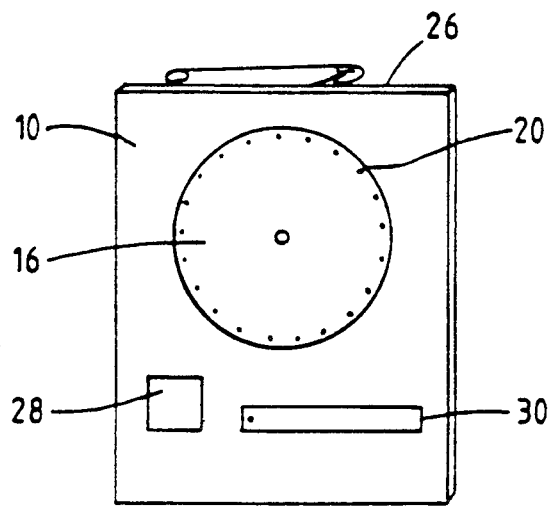

In FIG. 3, the porous detection layer 16 is also circular, but a series of entry apertures 20 are positioned round its periphery. Alternatively, a continuous circumferential entry aperture could have been provided. This device has the advantage that a near linear relationship exists between the developing (decreasing) spot radius and the gas concentration. The device also includes other features; a safety pin 26 for attachment to a user's clothing; a moisture sensitive area or test region 28 to show validity of the device; and an oxygen sensitive region 30 (open to the atmosphere at one end) to give a measure of the exposure time of the device.

Figure 4:
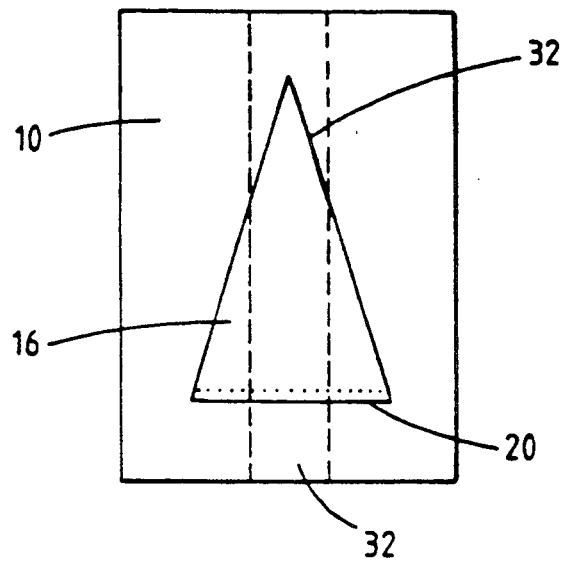

In FIG. 4, the porous detection layer 16 is in the form of an isosceles triangle or a sector of a circle, and a slit or multiple hole entry aperture 20 is positioned along the short side. The plastics sheet 10 is generally opaque, except for a viewing lane 32. A feature of this device is that the reactive area of the detection layer 16 decreases with increasing distance from the entry aperture, providing a near linear relationship between the moving boundary and the gas concentration. This results in a device which is more sensitive at higher analyte concentrations than the disc or linear versions shown in FIGS. 1 to 3.

Figure 5:
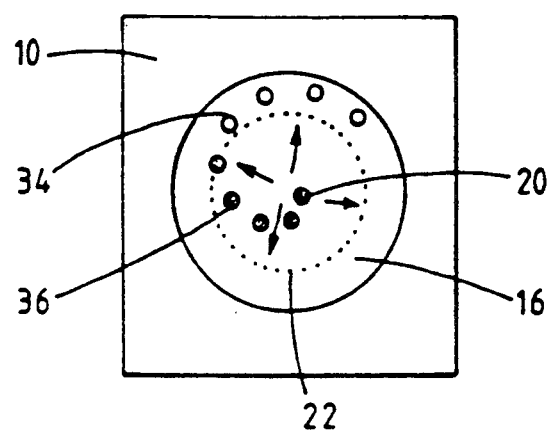

In FIG. 5, the plastics sheet 10 is opaque except for small viewing areas marked as 34 and 36. The porous detection layer 16 has the form of a circular disc with an entry aperture 20 at its center. The device has been exposed to analyte, and the resulting moving boundary 22 is shown dotted. The viewing aperture 36 is within this boundary and is therefore colored. The viewing aperture 34 is outside the boundary and is therefore colorless. By noting how many of the viewing apertures, which are arranged in a spiral, are colored, the user knows what is the cumulative dose of analyte from the surrounding atmosphere.

Referring to FIG. 6, a porous anodic oxide sheet 16 constitutes a detection layer, there is a contiguous spreading layer 18 and the two are sandwiched between plastics sheets 40 and 42 which are heat-sealed together round their edges. An entry aperture (not shown) is positioned cit one end; or may be provided by cutting off one end of the device.

Figure 6A:
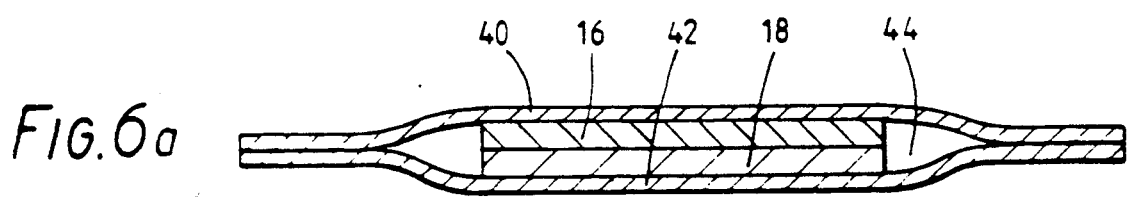
FIGS. 6a, 6b and 6c are diagrammatic sections through alternative devices.

In FIG. 6a, an air gap 44 may allow transport of analyte more rapidly than does the spreading layer 18, i.e. may permit access of analyte to the detection layer 16 other than via the spreading layer 18, so the observed moving boundary 22 may not be a straight one.

Figure 6B:
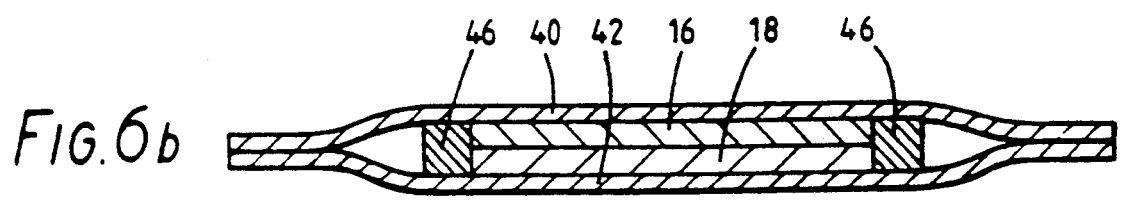

In FIG. 6b, a gasket 46 is positioned round the edges of the two layers 16, 18, and prevents leakage of analyte.

Figure 6C:
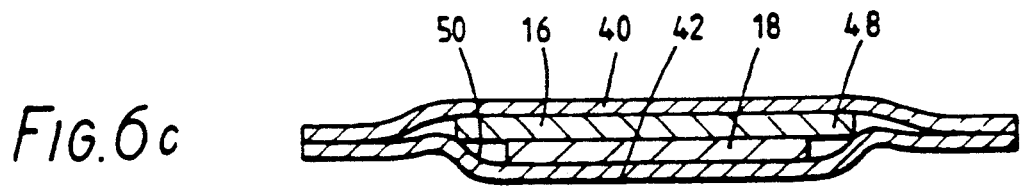

In FIG. 6c, the detection layer 16 is larger than the spreading layer 18 and overlaps it at 48. The air gap 50 that remains round the spreading layer is smaller and does not permit significant leakage of analyte.

Figure 7A:
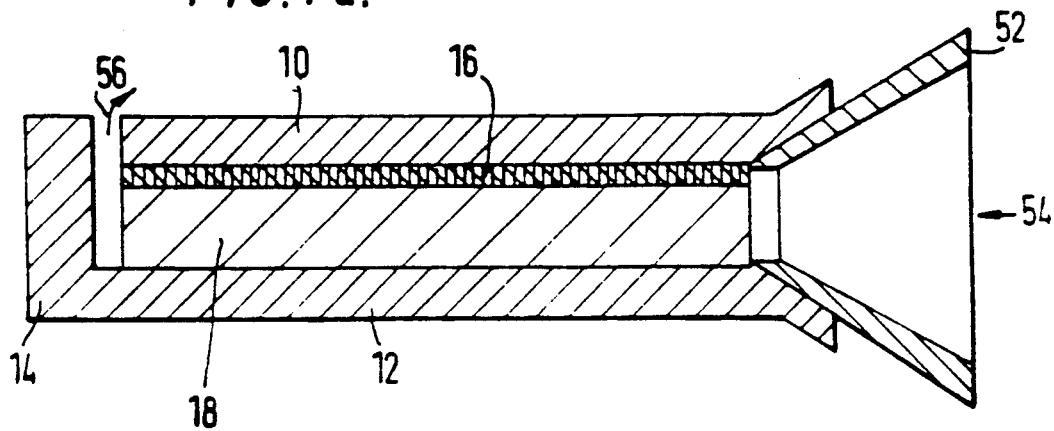
FIGS. 7a and 7b are section and plan views of a flow-through device.
Figure 7B:
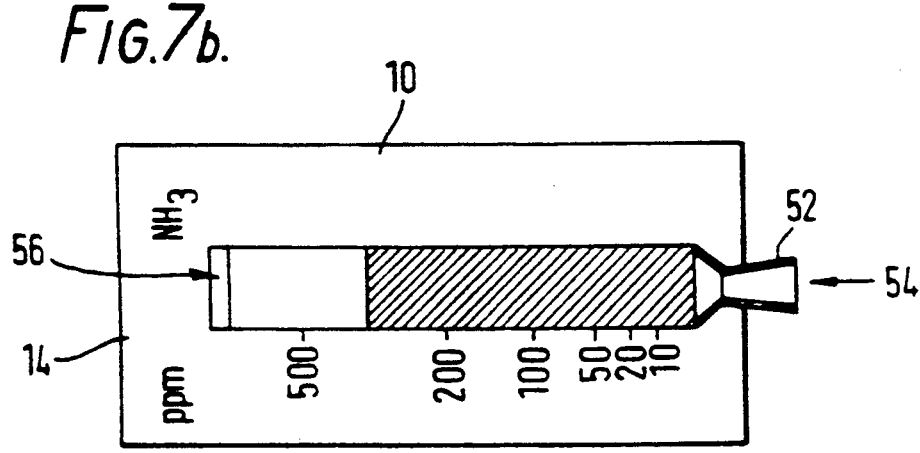

Referring to FIG. 7, a container comprises two flexible sheets 10, 12 of transparent plastics material moulded together at 14 round their periphery. Sandwiched between the two sheets are a porous detection layer 16 and a spreading layer 18. The porous detection layer 16 is an impregnated anodic aluminium oxide membrane. The spreading layer 18 is an air gap 0.1–1.0 mm thick, but could alternatively have been a filter paper. An inlet adapter 52 (a circular syringe type fitting) defines an inflow 54 for sample gas. A vent 56 is provided for gas that has passed through the spreading layer 18. A pressure difference can be maintained between the inflow 54 and the vent 56 by any convenient means (not shown). In use, a predetermined volume of fluid (gas) is pumped through the device; the position of the moving boundary indicates the concentration of the analyte in the fluid.

Figure 8:
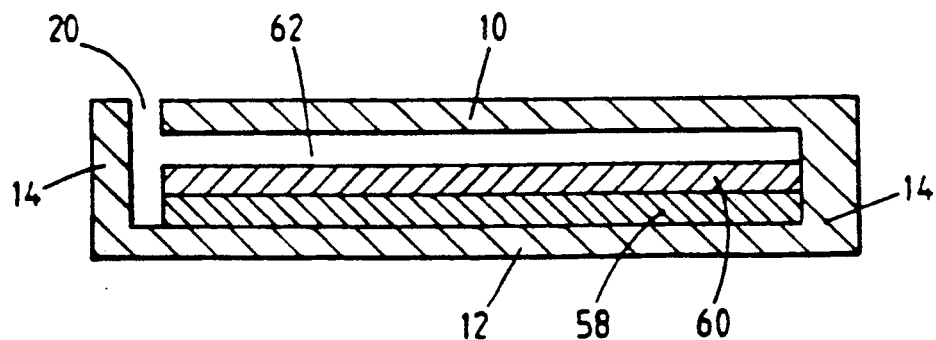
FIG. 8 is a section similar to FIG. 1b of another embodiment of the invention.

Referring to FIG. 8, a container comprises two flexible sheets 10, 12 of transparent plastics material moulded together at 14 round their periphery. Sandwiched between the two sheets are a detection layer 60 and a spreading layer 62. The detection layer 60 is an anodic aluminium oxide film which is still attached to the aluminium metal substrate 58 on which it was formed. The spreading layer 62 is an air gap, through a different transparent or translucent spreading layer would have been possible.

EXAMPLE 1

In experiments to demonstrate the invention the following sheets were used:

a) Anodic aluminium oxide membranes of dimensions 70×10 mm and 60 μm thick with substantially cylindrical pores 0.2 μm diameter.

b) Tape-cast membranes of dimensions 70×10 mm and 280 μm thick, of partly sintered aluminium oxide particles with a pore size of 0.48 μm.

c) Commercially available 3MM Chr chromatography paper (Whatman), cut into strips 70×10 mm. The filter paper was used in some experiments as the detection layer and in others as the spreading layer.

Sheets to be used as the detecting layer were immersed in 0.5% (w/v) bromophenol blue solution in 90% ethanol (10% water) containing 0.4% citric acid as buffering agent, and allowed to dry in air. The resulting sheets were then sandwiched, together with a spreading layer c) between two sheets of transparent plastics material. The combined sheets then had a slit 0.2–1 mm wide by 10 mm cut across the end of the detecting layer. Exposure of the device to ammonia vapor, resulted in the yellow detecting layer developing a blue region from the end adjacent to the slit, the length of the blue region depending on the degree of exposure to the ammonia.

Quantitative measurements were made using the above experimental set up with three different combinations of two of the above sheets a, b, or c as follows:

i) ac. Thus the anodic oxide membrane a is the detection layer and the filter paper c is the spreading layer.

ii) bc. The filter paper c is the spreading layer.

iii) cc. The filter paper c is the spreading layer.

Each device was exposed to gas containing 5000 ppm ammonia vapor for 1 hour. The results obtained are summarized in the following table.

|  | Detection/Spreading Layer Combination | | |
| --- | --- | --- | --- |
|  | i | ii | iii |
| Distance travelled in unit time (relative) | 10 | 9.6 | 8 |
| Relative time taken to set distance | 1 | 1.09 | 1.56 |
| Color Intensity | 10 | 2 | 10 |
| Resolution | 8 | 10 | 8 |
| Thickness of impregnated layer (μm) | 60 | 280 | 300 |
| Relative Reagent Quantity required | 1 | 4 | 4 |

Color intensity and resolution are both rated on a subjective scale from 0 (worst) to 10 (best). When used as detecting layers, the anodic sheet a) and the falter paper c) gave good resolution and excellent color intensity; while the tape-cast sheet b) gave excellent resolution but lower color intensity. Partly due to differences in thickness and the optical properties of the anodic membrane, the amount of chemical reagent (bromophenol blue) required for the anodic sheet a) was much less than for the other two sheets.

EXAMPLE 2

The anodic and tape-cast refractory sheets a) and b) are normally fragile. However, this need not be a problem when they are used in devices according to this invention. Combinations i) and ii) as described in Example 1 resemble credit cards, which were then damaged by folding and crushing manually. When tested subsequently, these devices gave results almost the same as the devices before damage; the main difference was that the moving boundary was found to move some 10% faster after damage than before.

EXAMPLE 3

Anodic aluminium oxide membrane sheets a) were immersed in 0.2M barium hydroxide solution containing 0.2% w/v phenolphthalein, and allowed to dry in air. Using a second unimpregnated anodic aluminium oxide sheet a) as the backing layer the two membranes were sandwiched between two layers of plastics and a slit 0.2–1 mm wide by 10 mm cut across the end of the detecting layer. Due to the parallel pore nature of the anodic membrane, no lateral diffusion can occur within the membrane, however, in the present example the narrow but uniform air-gap between the two anodic layers allows gas to diffuse into the device in a controlled manner. Exposure of the device to carbon dioxide gas concentrations results in the disappearance of the pink coloration of the strips the length of the colorless region being dependent on the degree of exposure.

EXAMPLE 4

Circular anodic aluminium oxide membrane sheets 43 mm in diameter 60 μm thick, were immersed in 0.3M copper sulphate solution, and allowed to dry in air. The resulting sheets were then sandwiched with a 45 mm diameter backing layer of 3MM Chr chromatography paper, between two sheets of transparent plastics material (one with a 0.2-1 mm hole in the middle) and clamped together in a membrane holder. Exposure of the device to hydrogen sulphide resulted in the appearance of a dark brown central spot the diameter of which depended on the degree of exposure to hydrogen sulphide. When another of the devices was exposed to ammonia a dark mauve central spot was formed, the diameter of which increased in proportion to the exposure to the gas. Hydrogen sulphide has also been detected and quantitated in the same way using lead acetate in place of the copper sulphate. This example was performed using both symmetric and asymmetric porous anodic membranes.

EXAMPLE 5

Further experiments, performed as described in Examples 3 and 4, have been used to detect nitrogen dioxide, ethanol, carbon monoxide and hydrogen chloride. The devices were based upon the credit card configuration using an anodic membrane having a 0.2 μm pore size backed with a variety of different spreading layers.

EXAMPLE 6

By constructing a modified device based upon Example 1 it has been possible to demonstrate a pumped rather than diffusion based device. The incorporation of a tapered tube inlet to the device with a second vent at the opposite end to allow gas to escape, enables a known volume of gas to be pumped through the device and the gas concentration to be determined from the position of the colored border. Utilizing bromophenol blue/citric acid impregnated strips prepared as in Example 1a in conjunction with a 0.2 mm gap as the spreading layer, resulted in development of a blue region 60 mm in length upon exposure to 500 ml of 500 ppm ammonia in air. The position of the colored border is related to the concentration of analyte and the volume of gas pumped through the device.

EXAMPLE 7

An anodic aluminium oxide membrane sheet was coated on one side with a titania sol (derived from titanium isopropoxide) excess sol was removed and the coated membrane dried in air. This coated membrane was sandwiched, with a porous spreading layer, between two sheets of transparent plastic material. Immediately after lamination the sol layer on the membrane surface exhibited an orange coloration which changed to black/green on exposure to light. The combined sheets then had a slit 0.1-1 mm wide by 10 mm cut across the detecting layer. Exposure of the device to an $O_2$ atmosphere resulted in the black/green detecting layer developing an orange region from the end adjacent to the slit, the length of the orange region depending on the degree of exposure to $O_2$.

EXAMPLE 8

By impregnating an anodic aluminium oxide membrane sheet with lead nitrate solution ($\approx 50$ μl of 0.1M $Pb(NO_3)_2$ and laminating together with a strip of 3MM Chr chromatography paper, a device was produced that allowed detection of sulphides in aqueous solutions. The device is operated by immersing the open end into the sample solution and allowing capillary action to fill the device from the bottom. At the top of the laminated strip is a second smaller vent to allow displaced air to escape. Immersion in a 0.02M sodium sulphide solution resulted in a dark brown region (lead sulphide) deposited within the lower 11 mm of the strip. The height (length) of the colored border relates to the aqueous concentration of sulphides present.

EXAMPLE 9

Strips of Whatman 3MM Chr chromatography paper were impregnated with bromophenol blue/citric acid solution as described in Example 1c). These were then laminated into devices incorporating a 0.5 mm gap as the spreading layer allowing diffusion into the device. Exposure to 5000 ppm ammonia followed the anticipated square root relationship of time to distance travelled, and achieved a relative speed of 2.5× the device fabricated as in Example 1i).

EXAMPLE 10

COMPARISON OF SPREADING LAYERS: Example 1i) was repeated using the detection layer of Example 1a) and the spreading layers listed in the following table. A Whatman 3MM paper was used as the standard and the results expressed as a ratio to the rate of spread in the test strip to that in the standard material.

Relative rates of different spreading layers

| Strip Type | Relative rate (3MM = 1) |
| --- | --- |
| Whatman GD-1 | 2.56 |
| Porex plastic sinter | 2.10 |
| Whatman GF/F | 1.73 |
| 0.20 mm gap | 1.24 |
| Whatman 3MM | 1.00 |
| Whatman 1Chr | 0.67 |
| Anopore 0.2 μm | 0.26 |
| Anopore 0.02 μm | 0.10 |

Resolution is equal to or better than length-of-stain tubes.

We claim:

1. A moving boundary gas detection device for detecting a gaseous analyte, which device comprises an impervious container having at least one fluid entry aperture and containing two contiguous layers said contiguous layers comprising:
   a detecting layer which is an anodic aluminum oxide sheet having pores extending transversely from one major face of the sheet to the other and comprising a reagent to generate a signal by a reaction initiated by a gaseous analyte,
   and a spreading layer permeable by the gaseous analyte positioned such that gaseous analyte entering the impervious container spreads within the spreading layer, wherein said spreading layer determines the movement of a moving boundary resulting from the reaction in said detection layer.
2. A device as claimed in claim 1 wherein said spreading layer includes pores forming a plurality of tortuous paths.
3. A device as claimed in claim 1, wherein the detection layer and the spreading layer are both elongated sheets positioned in the impervious container with one end adjacent the at least one fluid entry aperture.
4. A device as claimed in claim 1, wherein the impervious container comprises two flexible sheets impermeable to the gaseous analyte joined round their periphery and enclosing the detection layer and the spreading layer between them.

5. A device as claimed in claim 4, wherein the flexible sheet overlying the detection layer is transparent or translucent.

6. A device as claimed in claim 4, wherein the detection layer and the spreading layer are both elongate sheets positioned in the impervious container with one end adjacent the at least one entry aperture.

7. A device as claimed in claim 6, wherein a gasket surrounds the edges of the two flexible sheets.

8. A device as claimed in claim 6, wherein one flexible sheet is larger in area than the other and overlaps the other at the edges.

9. A device as claimed in claim 1, wherein the spreading layer is such that gaseous analyte entering the impervious container spreads by diffusion within the spreading layer.

10. A device as claimed in claim 1, wherein the impervious container also has an outlet, for operation in a pumped mode.

11. A device as claimed in claim 1, wherein the spreading layer is such that gaseous analyte entering the impervious container spreads by capillary action within the spreading layer.

* * * * *